United States Patent [19]
Sunderland

[11] Patent Number: 5,971,991
[45] Date of Patent: Oct. 26, 1999

[54] CATHETER DRIVER

[76] Inventor: Mark Sunderland, P.O. Box 7255, 250 Durocher Street, Ottawa, ON, Canada, K1L 8E3

[21] Appl. No.: 09/074,218

[22] Filed: May 7, 1998

[30] Foreign Application Priority Data

May 7, 1997 [CA] Canada ................................. 2204779

[51] Int. Cl.⁶ ..................................................... A61F 11/00
[52] U.S. Cl. ......................... 606/108; 606/130; 606/159; 604/93; 604/94; 604/95
[58] Field of Search ..................... 606/108, 130, 606/159, 191; 604/93–95, 174, 178, 179

[56] References Cited

U.S. PATENT DOCUMENTS

| | | | |
|---|---|---|---|
| 5,253,643 | 10/1993 | Price | 606/174 |
| 5,601,568 | 2/1997 | Chevillon et al. | 606/108 |
| 5,827,306 | 10/1998 | Yoon | 606/159 |

FOREIGN PATENT DOCUMENTS

| | | |
|---|---|---|
| 1318824 | 6/1993 | Canada . |
| 2207995 | 7/1996 | Canada . |
| 2213923 | 2/1998 | Canada . |
| WO 96/20026 | 7/1996 | WIPO . |

*Primary Examiner*—Michael Buiz
*Assistant Examiner*—Lien Ngo
*Attorney, Agent, or Firm*—Rader, Fishman & Grauer PLLC

[57] ABSTRACT

Disclosed is a catheter driver for use with a flexible, elongated catheter having opposite ends and an intermediate portion and intended for manipulation by a user during insertion of the catheter into the body of a patient. The driver of the invention is constructed for one-handed operation making it easier for the user to guide the catheter into the patient while operating the driver and obviating the need for relinquishing control of the catheter for advancing the driver. The driver includes an elongated body for being gripped by a band of the user. The body having a longitudinal axis and forward and rear ends, a longitudinally extending recess in the body for slidably receiving the intermediate portion of the catheter; and a lock structure operable by the same hand of the user for locking the intermediate portion of the catheter in the recess to allow application of axial thrust to the catheter.

11 Claims, 3 Drawing Sheets

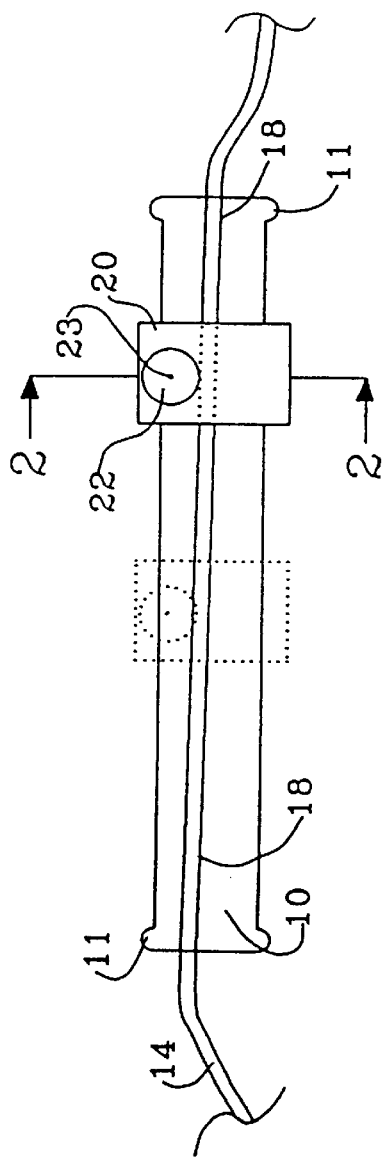
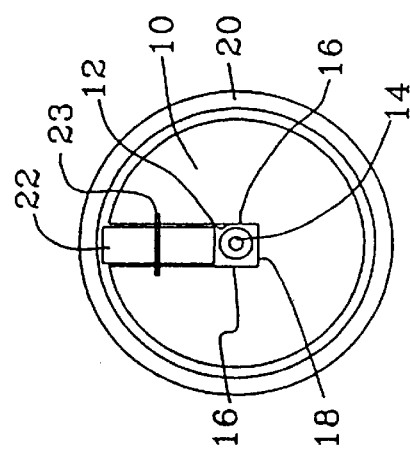
FIG 1A
FIG 1B

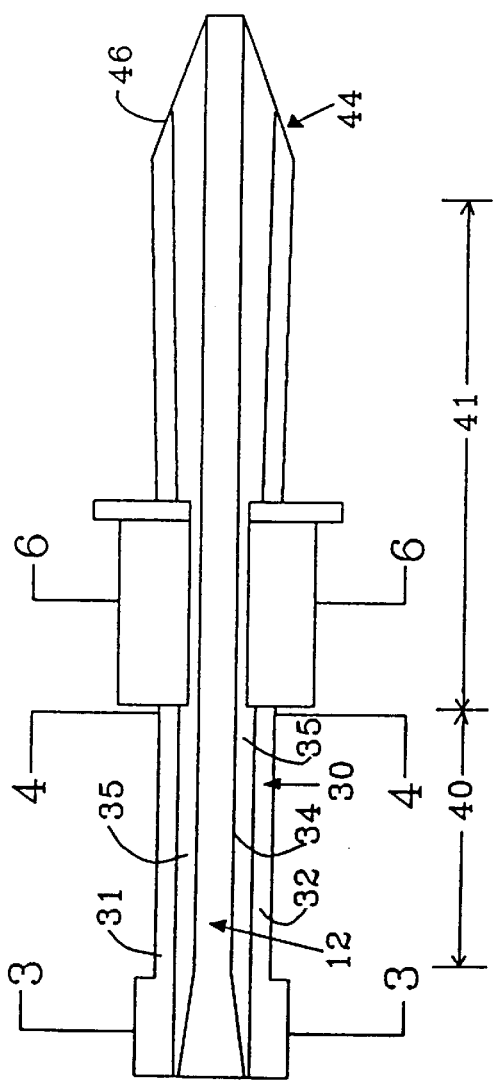
FIG 2
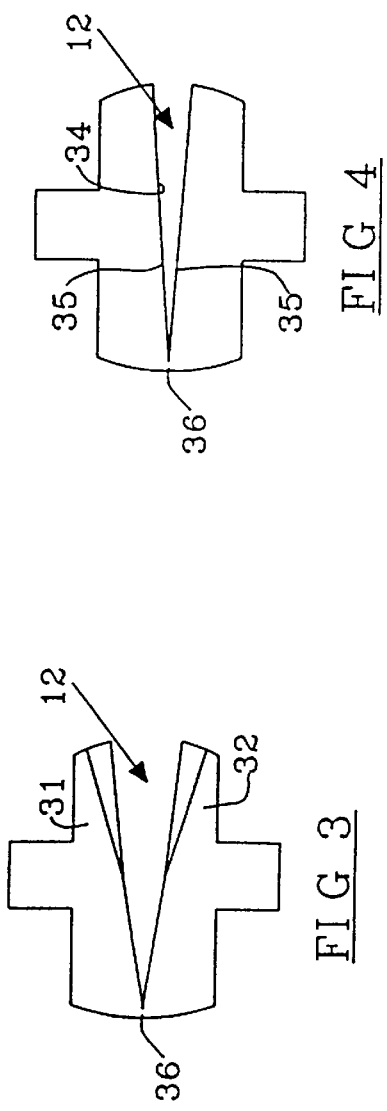
FIG 3
FIG 4

CATHETER DRIVER

FIELD OF THE INVENTION

The invention relates to catheters, and in particular, to tools for the handling and driving of catheters. More particularly, the invention relates to devices used for the pushing of a catheter during insertion thereof into the body of a patient.

BACKGROUND OF THE INVENTION

Catheters are often used in exploratory and testing procedures to avoid invasive surgical procedures. Access to the patient's body is usually gained through existing body orifices, small incisions or punctures. In use, the catheter is progressively driven into the patient's body by pushing it along existing body cavities, tubes, ducts, or blood vessels to the target area within the patient's body. To avoid damage to body tissues, the catheter must be highly flexible. Furthermore, catheters are normally of small diameter to allow their use within small conduits and to increase flexibility. For example, the diameter of a catheter for use in a testing procedure is normally with the range of 0.10 mm to 4 mm. This small diameter makes manipulation of the catheter by the operator difficult, especially when working under aseptic conditions with talcum-treated latex gloves. Moreover, the light-weight and thin, wire-shaped portion of the catheter which remains external to the patient's body is naturally unstable and awkward to handle, in particular during insertion of the catheter deeper into the patient's body which requires pushing of the catheter by application of axial thrust to the portion of the catheter still outside the patient's body.

To overcome these problems and facilitate control and handling of a thin, highly-flexible catheter, it has been suggested to employ a modified pin vice having a handle portion provided with an axial through bore for insertion of the catheter so that it can be gripped by releasably closeable jaws of a chuck at the front end of the vice. The catheter is threaded through and tightly gripped by the jaws in the closed condition of the chuck. The catheter is progressively insetted into the body of the patient by pushing the catheter with the pin vice. Such a device provides the operator with substantially improved feel and grip of the catheter. However, this device is not practical in most applications and not cost effective. To change the position of the vice on the catheter, the chuck must be rotated relative to the body of the vice for opening and closing of the jaws. The observed technical weakness is that for this operation, the operator must use both hands, one to hold the handle and the other one to open or tighten the chuck. This means the physician setting the catheter, unless assisted by another person, cannot maintain control of the catheter's position and orientation in the patient's body, possibly leading to internal injury or damage to the catheter. The procedure is also time intensive. Moreover, the pin vice cannot be applied to the catheter after insertion thereof into the patient. It can also not be removed after insertion of the catheter is complete and may interfere with the subsequent testing procedure. In addition, the use of a pin vice is relatively costly since it normally does not withstand repeated sterilization rendering it unsuited for single use in aseptic environments.

SUMMARY OF THE INVENTION

Thus, it is an object of the invention to provide a device for manipulating a catheter during insertion into a patient which device is more flexible in its application and adapted for single-handed use.

It is another object to provide a catheter driver or handle which can be applied to or removed from the catheter even when the front end of the catheter is not accessible.

It is a further object to provide a catheter driver or handle which is adapted for use with a significant range of catheter diameters.

These objects are now achieved with a catheter driver in accordance with the invention having an elongated body for being gripped by a user's hand, a longitudinally extending recess in the grip for slidably receiving a portion of the catheter intermediate the catheter ends, and lack means operable by the same hand of the user for releasably locking the portion of the catheter in the recess to allow application of axial thrust to the catheter.

The catheter driver preferably further includes a means for maintaining the intermediate portion of the catheter in the recess to prevent accidental detachment of the driver from the catheter when the driver is released from the user's hand.

The lock means is preferably a means for forcing the portion of the catheter against a wall of the recess to create the friction required to prevent sliding movement of the catheter in the recess upon application of axial thrust.

The means for maintaining preferably removably maintains the catheter in the recess.

BRIEF DESCRIPTION OF THE DRAWINGS

Preferred embodiments of the catheter driver in accordance with the invention will now be described in detail by way of example only and with reference to the appended drawings wherein:

FIG. 1a is a schematic view of a first preferred embodiment of the catheter driver in accordance with the invention;

FIG. 1b is a cross-section through the embodiment of FIG. 1a and taken along line 2—2;

FIG. 2 is a top view of a second preferred embodiment of the catheter driver in accordance with the invention with a catheter inserted therein;

FIG. 3 is a cross-sectional view of the body of the catheter driver shown in FIG. 2 and taken along line 3—3;

FIG. 4 is a cross-sectional view of the body of the catheter driver shown in FIG. 2 and taken along line 4—4;

DETAILED DESCRIPTION OF THE PREFERRED EMBODIMENTS

Figure 5:
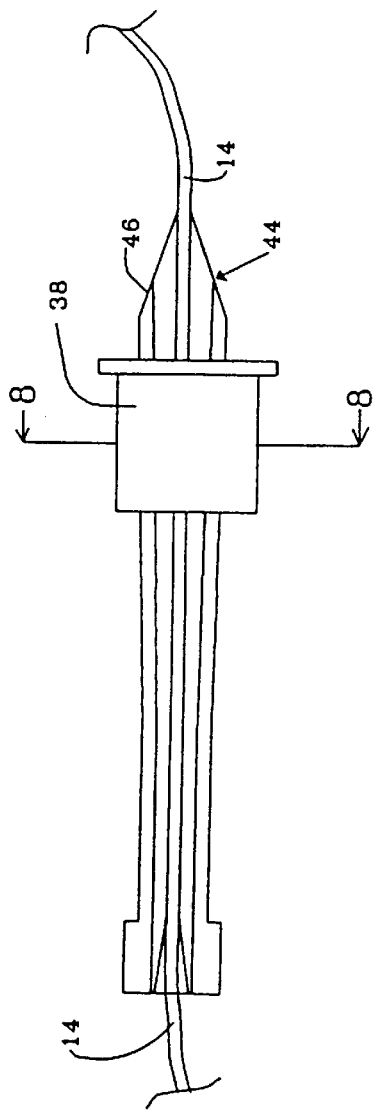
FIG. 5 is a top view of the catheter driver shown in FIG. 2 in the catheter locking condition.

Referring now to the attached figures, a catheter driver in accordance with the invention includes a body 10 provided with a longitudinally extending recess 12 for receiving an intermediate portion of a catheter 14 (only partially shown) and a structure for locking the catheter in the recess against longitudinal sliding movement.

In the preferred embodiment illustrated in FIGS. 1a and 1b, the catheter driver in accordance with the invention includes a body 10 of substantially cylindrical cross-section and having a recess 12 in the shape of a longitudinally extending, U-shaped groove with side walls 16 and a base wall 18. The base wall is inclined relative to a longitudinal axis (not shown) of the body 10. The structure for locking the catheter in the groove is a sleeve 20 which is slidably fitted around the body 10 and a wheel 22 rotatably affixed to the sleeve in an orientation such that the axis 23 of the wheel extends transverse to the groove and the plane of the wheel is parallel with the side walls 16 of the groove. The sleeve 20 is slidable along the body 10 of the driver between a rearward position as shown in full lines in FIG. 1a and a forward position as shown in broken lines in FIG. 1a. The axis 23 of the wheel 22 is sufficiently spaced from the base wall 18 at the rearward position of the sleeve 20 to allow insertion of a catheter therebetween. The maximum spacing of the wheel circumference from the base wall 18 is about equal to the diameter of the largest catheter intended for use with the driver. The angle of inclination of the base wall 18 relative to the longitudinal axis of the body 10 is selected such that the wheel substantially engages the base wall 18 when the sleeve is in the forward position. During sliding of the sleeve 20 from the rearward to the forward position, the spacing between the wheel and the base wall 18 progressively decreases due to the inclination of the base wall relative to the axis of body 10. The axial ends of the body are each provided with a ridge 11 preventing the slider sleeve 20 sliding off the body 10 at the ends thereof.

During use, the catheter 14 is threaded through the opening defined between the wheel 22 and the base wall 18 of the groove with the sleeve 20 in the rearward position. To lock the catheter 14 in the groove, the slider sleeve 20 is pushed towards the forward position by the user and by a digit of the same hand which grips the body 10, most likely the thumb. Thus, the driver is constructed for one-handed operation. The sleeve 20 is pushed forward until the wheel 22 pushes the catheter against the base wall 18 and sufficient friction is created to prevent axial sliding of the catheter in the groove to allow application of axial thrust to the catheter. Should the catheter slip during the application of thrust, the sleeve simply has to be pushed forward some more until the sliding stops. To ensure reliable locking of the catheter in the recess, the base wall can be provided with a high friction coating (not illustrated) generally known in the art of medical equipment. To prevent damage to the catheter upon excessive forward force on the sleeve, a resilient cushioning layer (not shown) is provided on the base wall 18 and/or the outer circumference of the wheel 22. In the most preferred embodiment, the cushioning layer is made of a resilient, high-friction material.

Figure 7:
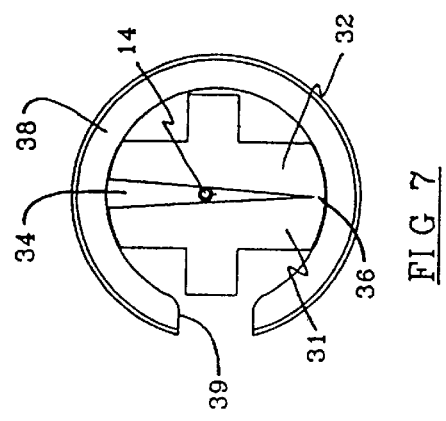
FIG. 7 is a cross-sectional view of the body of the catheter driver shown in FIG. 5 and taken along line 8—8.
Figure 6:
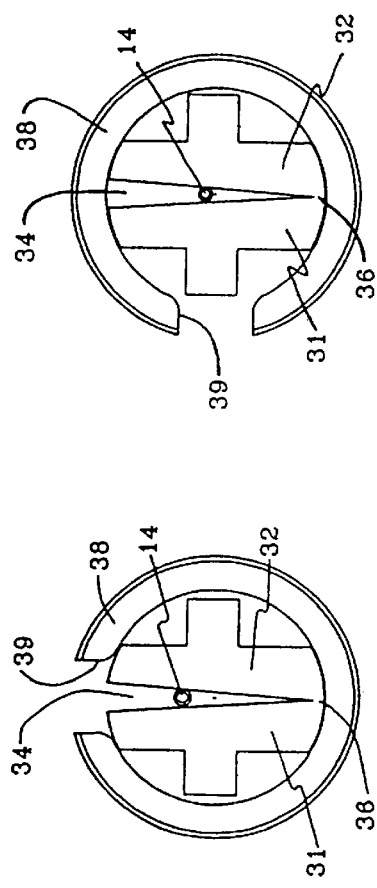
FIG. 6 is a cross-sectional view of the body of the catheter driver shown in FIG. 2 and taken along line 6—6.

In the second preferred embodiment of the catheter driver of the invention as shown in FIGS. 2 to 7, the driver includes a body 30 consisting of two halves 31, 32 which define a longitudinally extending recess 12 in the shape of a V-shaped groove 34 having side walls 35 as best seen in FIGS. 3 and 4. The body halves are connected by a longitudinally extending, flexible hinge 36. The structure for locking the catheter 14 in the driver is provided in this embodiment by the flexible hinge 36 and the opposing side walls 35. The hinge 36 permits the user to press the body halves 31, 32 against one another thereby forcing the catheter against the side walls 35 of the groove 34 and providing sufficient friction to permit the application of axial thrust to the catheter without sliding of the catheter in the groove. The hinge 36 has internal resilience to normally force the body halves 31, 32 apart to open the groove. This allows locking and unlocking of the catheter in rapid succession for quick insertion of the catheter into the body of the patient. The advantage of this driver over the pin vice is that the catheter can be clasped at any moment during a testing procedure since it does not need to be threaded through the device. The driver is preferably produced from a suitable thermoplastic polymer known to the person skilled in the art which would allow the body 30 and the hinge to be made of the same material while having sufficient flexibility to enable the construction of a "live" hinge extending along the length of the underside of the body 30 which includes sufficient resiliency to normally force the body halves apart at their unattached edges.

The driver of this embodiment further includes an annular slider sleeve 38 provided with a slot 39 extending parallel to the axis of the body 30. The sleeve 38 is both slidable along the body 30 and rotatable thereon about the axis of the body and thereby allows fastening of the driver to the body 10 against accidental detachment. This is achieved by rotation of the sleeve 38 to an angular position wherein the axially extending slot 39 does not overlap the groove 34. The width of the slot 39 is selected to permit insertion of a catheter 14 into the groove 34. The slider sleeve 38 also functions to maintain the body halves 31, 32 in the catheter locking condition. To this end, the body 30 includes a cylindrical rearward portion 40 and a leading portion 41 which has a progressively increasing diameter towards a front end 44 of the body. The front end 44 is provided with a nose cone 46 for ease of handling. When the sleeve 38, which has a uniform inside diameter, is pushed forward over the diverging forward portion 41 of the body 30, the groove 34 in the handle progressively closes without the user having to manually force the body halves 31, 32 against one another. The angle of taper of the leading portion 41 is preferably selected such that the sleeve 38 will remain stationary on the body due to friction therebetween, if the catheter body 30 is released by the user while the catheter is locked between the body halves.

During use, the sleeve is withdrawn over the cylindrical rearward portion 40 of the body 30. The slot 39 in the sleeve 38 is centered over the groove 34. The catheter is then laid into, the groove 34 and the sleeve 38 rotated 90 degrees to the left or right to position the sleeve gap 39 over one of the body halves to completely encase the catheter against accidental detachment from the handle. The catheter is locked in the driver against axial movement during application of axial thrust to the catheter by the user closing the hand which grips the body 30 of the driver. When the sleeve is pushed forward over the diverging portion 41 of the body 30 and by the same hand of the user, most likely by the thumb, the groove 34 closes whereby the catheter is locked within the groove even when the driver is released by the user.

The rear end of the body 30 includes a radial projection 44 to restrict the sleeve 38 from becoming accidentally detached from the handle. Removal of the sleeve 38 by sliding it off the leading end of the body is not possible due to the enlargement of the leading end. To reduce material cost and for molding purposes, the body 30 has a substantially star-shaped cross-section with the central groove 34 separating two body halves 31, 32 respectively provided with lateral, longitudinally extending handle ribs 46. The width and height of the ribs 46 is preferably selected such that they respectively extend partially into the slot 39 of the sleeve 38 when the latter is in the catheter fastening position where the slot 39 does not overlap the groove 34, as shown for example in FIG. 7. This provides for a latching of the sleeve 38 in the catheter holding position (see FIG. 7). The groove 34 is preferably outwardly tapered towards the rear end of the body (see FIGS. 3–5) to facilitate entry of the catheter 14 into the body during sliding of the driver therealong and to prevent damage to the catheter 14 during bending. Changes and modifications in the specifically described embodiments can be carried out without departing from the scope of the invention which is intended to be limited only by the scope of the appended claims.

The embodiments of the invention in which an exclusive property or privilege is claimed are defined as follows:

1. A catheter driver for use with a flexible, elongated catheter having opposite ends and an intermediate portion and intended for manipulation by a user during insertion of the catheter into the body of the patient, the driver comprising:

an elongated body for being gripped by a hand of the user, the body have a longitudinal axis and forward and rear ends;

a longitudinally extending recess in the body for slidably receiving the intermediate portion of the catheter, and lock means for locking the intermediate portion of the catheter in the recess to allow application of axial thrust to the catheterperiod, the lock means being normally in an at rest position wherein it permits sliding movement of the intermediate portion in the recess and movable by the same hand of the user to a locking position wherein the lock means locks the intermediate portion.

2. A catheter driver as defined in claim 1, wherein the recess is a groove extending a length of the body.

3. A catheter driver as defined in claim 1, wherein the recess is a groove having a bottom wall being inclined relative to the axis of the body; and the lock means is a sleeve slideable along the body and having means for pushing the intermediate portion of the catheter into the groove, the means for pushing extending a preselected distance into the groove, the preselected distance and an angle of inclination of the base wall being selected such that the intermediate portion of the catheter is forced against the base wall by the means for pushing upon forward movement of the sleeve along the body.

4. A catheter driver as defined in claim 1, wherein the body is divided into a pair of body halves each having first and second longitudinal edges, which body halves together define the recess therebetween, the lock means being a resilient hinge resiliently connecting the respective first edges of the body halves for movement of the second edges of the body halves to and from one another between an open position wherein the second edges are sufficiently spaced apart to permit insertion of the intermediate portion of the catheter therebetween and a closed position wherein the second edges are spaced at a relatively smaller distance and the intermediate portion is gripped between the body halves when the body halves are manually forced towards one another by the user.

5. A catheter driver as defined in claim 1, further including a means for releasably holding the intermediate portion in the recess to substantially prevent accidental detachment of the driver from the catheter when the driver is released by the user's hand.

6. A catheter driver as defined in claim 5, wherein the means for holding is a sleeve extending about and rotatable relative to the body, the sleeve having an axial slot for passage of the intermediate portion, the sleeve being rotatable between a release and insertion position wherein the slot is positioned to overlap the groove to permit insertion of the intermediate portion through the slot into the groove, and a holding position wherein the sleeve is rotated about the axis of the body and the slot no longer sufficiently overlaps the groove to permit insertion of the intermediate portion.

7. A catheter driver as defined in claim 6, further including a means for latching the sleeve in the holding position.

8. A catheter driver as defined in claim 7, wherein the means for holding is a radially protruding longitudinally extending rib on the body which radially extends at least partly into the slot when the sleeve is in the holding position.

9. A catheter driver as defined in claim 5, further including a means for maintaining the pair of body halves in the closed position upon release of the driver by the user.

10. A catheter driver as defined in claim 9, wherein the means for maintaining includes a sleeve extending about and slidable, along the body and a forward portion of the body having a progressively increasing diameter, the sleeve progressively forcing the body halves together upon forward sliding movement of the sleeve along the body and over the forward portion.

11. A catheter driver for use with a flexible, elongated catheter having opposite ends and an intermediate portion and intended for manipulation by a user during insertion of the catheter into the body of a patient, the driver comprising;

an elongated body for being gripped by a hand of the user, the body having a longitudinal axis and forward and rearward ends;

a longitudinally extending recess in the body for slidably receiving the intermediate portion of the catheter, and lock means operable by the same hand of the user for locking the intermediate portion of the catheter in the recess to allow application of axial thrust to the catheter, wherein the recess is a groove having a bottom wall being inclined relative to the axis of the body; and the lock means is a sleeve slidable along the body and having means for pushing the intermediate portion of the catheter into the groove, the means for pushing extending a preselected distance into the groove, the preselected distance and an angle of inclination of the base wall being selected such that the intermediate portion of the catheter is forced against the base wall by the means for pushing upon forward movement of the sleeve along the body.

\* \* \* \* \*